(12) United States Patent
Dawson et al.

(10) Patent No.: US 9,611,483 B2
(45) Date of Patent: Apr. 4, 2017

(54) VIRAL BASED TRANSIENT-EXPRESSION VECTOR SYSTEM THAT ALLOWS MULTIPLE APPLICATIONS

(71) Applicant: University of Florida Research Foundation, Inc., Gainesville, FL (US)

(72) Inventors: William O. Dawson, Winter Haven, FL (US); Svetlana Y. Folimonova, Winter Haven, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 839 days.

(21) Appl. No.: 13/761,845

(22) Filed: Feb. 7, 2013

(65) Prior Publication Data

US 2013/0219556 A1 Aug. 22, 2013

Related U.S. Application Data

(60) Division of application No. 13/207,731, filed on Aug. 11, 2011, now Pat. No. 8,389,804, and a continuation of application No. PCT/US2011/031671, filed on Apr. 8, 2011.

(60) Provisional application No. 61/445,105, filed on Feb. 22, 2011, provisional application No. 61/440,445, filed on Feb. 8, 2011, provisional application No. 61/321,970, filed on Apr. 8, 2010.

(51) Int. Cl.
*C12N 15/82* (2006.01)
*C12N 7/00* (2006.01)
*C12N 15/86* (2006.01)

(52) U.S. Cl.
CPC ........... *C12N 15/8203* (2013.01); *C12N 7/00* (2013.01); *C12N 15/86* (2013.01); *C12N 2770/00034* (2013.01); *C12N 2770/00043* (2013.01)

(58) Field of Classification Search
None
See application file for complete search history.

(56) References Cited

U.S. PATENT DOCUMENTS

| 8,389,804 B2 | 3/2013 | Dawson et al. |
| 2004/0029280 A1 | 2/2004 | Sosnowski et al. |
| 2004/0087537 A1 | 5/2004 | Federico |

FOREIGN PATENT DOCUMENTS

WO 2009099877 A2 8/2009

OTHER PUBLICATIONS

Folimonov et al. (J. of Virol. (2010) 84: 1314-1325).*
Voinnet et al., Trends in Genetics (2001) 17: 449-459.*
Peng et al. (J. of Virol. (2001) 75: 12153-12160).*
Folimonov et al. (J. of Virol. (2010) 84: 1314-1325; epub: Nov. 18, 2009).*
Ehrengruber, M.U. et al., "Semliki Forest virus vectors with mutations in the nonstructural protein 2 gene permit extended superinfection of neuronal and non-neuronal cells", Journal of Neurovirology, 2007, vol. 13, No. 4, abstract only.
Folimonova, S. Y. et al., "Infection with Strains of Citrus Tristeza Virus Does not Exclude Superinfection by Other Strains of the Virus", Journal of Virology, Feb. 2010, vol. 84, No. 3, pp. 1314-1325.
Childs, J.D., "Superinfection Exclusion by Incomplete Genomes of Bacteriophage T4", Journal of Virology, 1973, vol. 11, No. 1, pp. 1-8.
Tatineni et al., "Three genes of *Citrus tristeza* virus are dispensable for infection and movement throughout some varieties of citrus trees", Virology, 2008, vol. 376, pp. 297-307.
Voinnet et al., "RNA silencing as a plant immune system against viruses", Trends in Genetics, 2001, vol. 17, pp. 449-459.
Adams, R.H. et al., "BHK Cells Expressing Sindbis Virus-Induced Homologous Interference Allow the Translation of Nonstructural Genes of Superinfecting Virus", Journal of Virology, May 1985, vol. 54, No. 2, pp. 351-357.
Bratt, M.A., et al., "Specific Interference among Strains of Newcastle Disease Virus", Virology, 1968, vol. 35, pp. 395-407.
Dawson, W.O., et al., "A Tobacco Mosaic Virus-Hybrid Expresses and Loses an Added Gene", Virology, 1989, vol. 172, pp. 285-292.
Delwart, E.L., et al., "Role of Reticuloendotheliosis Virus Envelop Glycoprotein in Superinfection Interference", Journal of Viroloty, Jan. 1989, vol. 63, No. 1, pp. 273-280.
Donson, J. et al., "Systemic expression of a bacterial gene by a tobacco mosaic virus-based vector", Proc. Natl. Acad. Sci., Aug. 1991, vol. 88, pp. 7204-7208.
Dulbecco, R., "Mutual Exclusion Between Related Phages", Journal of Bacteriology, 1952, pp. 209-217.
Fulton, R.W., "Superinfection by Strains of Tobacco Streak Virus", Virology, 1978, vol. 85, pp. 1-8.
Geib, T., et al., Selective Virus Resistance Conferred by Expression of Borna Disease Virus Nucleocapsid Components, Journal of Virology, Apr. 2003, vol. 77, No. 7, pp. 4283-4290.
Hilf, M.E., et al., "Characterization of Citrus Tristeza Virus Subgenomic RNAs in Infected Tissue", Virology, 1995, vol. 208, pp. 576-582.
Hilf, M.E., et al., "Genetic Marker Analysis of a Global Collection of Isolates of *Citrus tristeza* virus: Characterization and Distribution of CTV Genotypes and Association with Symptoms", Virology, 2005, vol. 95, No. 8, pp. 909-***.
Hull, R. et al., Short Communications—Electron Microscopy on the Behavior of Two Strains of Alfalfa Mosaic Virus in Mixed Infections, Virology, 1970, vol. 42, pp. 773-776.
Karasev, A.V., et al., "Complete Sequence of the *Citrus tristeza* Virus RNA Genome", Virology, 1995, vol. 208, pp. 511-520.

(Continued)

*Primary Examiner* — Vinod Kumar
(74) *Attorney, Agent, or Firm* — Timothy H. Van Dyke; Beusse, Wolter, Sanks & Maire PLLC

(57) ABSTRACT

Disclosed herein are viral vectors suitable for transfection into woody trees for purposes of delivering and expressing beneficial genes. Specifically exemplified herein are vectors for transfecting citrus trees. The vectors allow for the expression of useful proteins, such as those that can protect the tree from disease. Specifically exemplified herein are methods of transfecting woody trees that allow multiple applications of vectors while avoiding superinfection exclusion.

1 Claim, 2 Drawing Sheets

(56) References Cited

OTHER PUBLICATIONS

Karasev, A.V., "Genetic Diversity and Evolution of Closteroviruses", Annu. Rev. Phytopathol., 2000, vol. 38, pp. 293-324.
Karpf, A.R., et al., "Superinfection Exclusion of Alphaviruses in Three Mosquito Cell Lines Persistently Infected with Sindbis Virus", Journal of Virology, Sep. 1997, vol. 71, No. 9, pp. 7119-7123.
Lecoq, H. et al., "Control of Zucchini Yellow Mosaic Virus in Squash by Cross Protection", Plant Disease, 1991, vol. 75, No. 2, pp. 208-211.
Lee, Young-Min et al., "Dual Mechanisms of Pestiviral Superinfection Exclusion at Entry and RNA Replication", Journal of Virology, Mar. 2005, vol. 79, No. 6, pp. 3231-3242.
Lu, R. et al., "Three distinct suppressors of RNA silencing encoded by a 20-kb viral RNA genome", PNAS, Nov. 2004, vol. 101, No. 44, pp. 15742-15747.
Pappu, H.R., et al., "Nucloetide Sequence and Organization of Eight 3 Open Reading Frames of the *Citrus tristeza* Closterovirus Genome", Virology, 1994, vol. 199, pp. 35-46.
Rabindran, S. et al., "Assessment of Recombinants That Arise from the Use of a TMV-Based Transient Expression Vector", Virology, 2001, vol. 284, pp. 182-189.
Slaman, R.N., "Protective Inoculation against a Plant Virus", Nature, Apr. 1, 1933, p. 468.
Satyanarayana, T., et al., "An engineered closterovirus RNA replicon and analysis of heterologous terminal sequences for replication", Proc. Natl. Acad. Sci., Jun. 1999, vol. 96, pp. 7433-7438.
Satyanarayana, T., et al., "Closterovirus Encoded HSP70 Homolog and p61 in Addition to Both Coat Proteins Function in Efficient Virion Assembly", Virology, 2000, vol. 278, pp. 253-265.
Satyanarayana, T. et al., "Amplification of Citrus Tristeza Virus from a cDNA Clone and Infection of Citrus Trees", Virology, 2001, vol. 820, pp. 87-96.
Satyanarayana, T. et al., "The p23 Protein of Citrus Tristeza Virus Controls Asymmetrical RNA Accumulation", Journal of Virology, Jan. 2002, vol. 76, No. 2, pp. 473-483.
Satyanarayana, T. et al., "Frameshift mutations in infectious cDNA clones of *Citrus tristeza* virus: a strategy to minimize the toxicity of viral sequences to *Escherichia coli*", Virology, 2003, vol. 313, pp. 481-491.
Shivprasad, S., et al., "Heterologous Sequences Greatly Affect Foreign Gene Expression in Tobacco Mosaic Virus-Based Vectors", Virology, 1999, vol. 252, pp. 312-323.
Singh, I.R., et al., "Multiple Mechanisms for the Inhibition of Entry and Uncoating of Superinfecting Semliki Forest Virus", Virology, 1997, vol. 231, pp. 59-71.
Steck, F.T. et al., "The Mechanism of Interference Between an Avian Leukosis Virus and Rous Sarcoma Virus", Virology, 1966, vol. 29, pp. 628-641.
Strauss, J.H. et al., "The Alphaviruses: Gene Expression, Replication and Evolution", Microbiological Reviews, Sep. 1994, vol. 58, No. 3, pp. 491-562.
Visconti, N., "Resistance to Lysis From Without in Bacteria Infected With T2 Bacteriophage", Journal of Bacteriology, 1953, vol. 66, pp. 247-253.
Walkey, D.G.A., et al., "Studies on the control of zucchini yellow mosaic virus in courgettes by mild strain protection", Plant Pathology, 1992, vol. 41 pp. 762-771.
Whitaker-Dowling, P. et al., "Superinfection Exclusion by Vesicular Stomatitis Virus", Virology, 1983, vol. 131, pp. 137-143.
Wildum, S., et al., "Contribution of Vpu, Env, and Nef to CD4 Down-Modulation and Resistance of Human Immunodeficiency Virus Type 1-Infected T Cells to Superinfection", Journal of Virology, Aug. 2006, vol. 80, No. 16, pp. 8047-8059.
Albiach-Marti, M.R. et al., "Sequences of Citrus Tristeza Virus Separated in Time and Space are Essentially Identical", Journal of Virology, 2000, vol. 74, No. 15, pp. 6856-6865.
International Search Report and Written Opinion, PCT/US2011/031671, Apr. 6, 2012, 16 pages.
Martin, S. et al., "Contribution of recombination and selection to molecular evolution of Citrus tristeza virus", Journal of General Virology, 2009, vol. 90, pp. 1527-1538.
Weng, Z., et al., "Persistent Infection and Promiscuous Recombination of Multiple Genotypes of an RNA Virus within a Single Host Generate Extensive Diversity", PLos ONE, Sep. 2007, Issue 9, e917, 9 pages.

\* cited by examiner

A   T36 CTV9R

B   Delta p33 T36CTV9R

C   T36/T68 hybrid construct with leader proteases substitution

FIG. 1

T36/T68 hybrid with the leader proteases substitution (L1L2 h)

| No. | Primary | Challenge |
|---|---|---|
| 1 | none | none |
| 2 | T36 | none |
| 3 | L1L2 h | none |
| 4 | T36 | L1L2 h |

VIRAL BASED TRANSIENT-EXPRESSION VECTOR SYSTEM THAT ALLOWS MULTIPLE APPLICATIONS

CROSS REFERENCE TO RELATED APPLICATIONS

This is a divisional application of U.S. patent application Ser. No. 13/207,731 filed Aug. 11, 2011, which is a continuation application of PCT/US2011/31671 filed Apr. 8, 2011. This application is related to U.S. Provisional Application No. 61/321,970; filed Apr. 8, 2010 and to U.S. Provisional Application No. 61/440,445; filed Feb. 8, 2011 and to U.S. Provisional Application No. 61/445,105 filed Feb. 22, 2011. Priority to such applications is claimed under 35 USC 119 & 120. The full disclosures of the related applications are incorporated herein in their entirety.

FIELD OF INVENTION

Primary embodiments of the invention relate to a virus-based transient expression vector that expresses foreign genes in trees for long periods of time that will allow the application of a similar vector to the same trees at the same time or at later times. Other embodiments relate to viral vector constructs and methods that enable avoidance of superinfection exclusion, and in turn multiple applications of vectors.

BACKGROUND

Virus-based transient-expression vectors are routine tools used in plant molecular biology laboratories throughout the world for rapidly expressing or silencing genes in plants. They also can be important tools in plant genomics to screen unknown sequences for function. Yet, available vectors have been developed from a limited number of rather similar viruses of herbaceous plants. Notable examples are the vectors based on Tobacco mosaic virus (TMV) (Dawson et al., 1989; Donson et al., 1991; Shivprasad et al., 1999; Rabindran and Dawson, 2001). Tree crops offer special challenges. Even if existing vectors could infect trees, the time required for systemic infection and analysis of the expressed genes in trees generally exceeds the stability of known virus-based vectors. Yet, the challenges of breeding restraints and the decades required for improving trees greatly increase the need for useful virus-based vectors.

Citrus tristeza virus (CTV) is a member of the complex Closteroviridae family that contains viruses with mono-, bi-, and tri-partite genomes transmitted by a range of insect vectors including aphids, whiteflies, and mealybugs (Bar-Joseph et al., 1979; Dolja et al., 1994; Agranovsky, 1996; Karasev, 2000). The long flexuous virions (2000 nm×10-12 nm) of CTV are encapsidated by two coat proteins: the major coat protein (CP) covering about 97% of the virion and the minor coat protein (CPm) completing encapsidation of the other terminus. The single-stranded RNA genome of CTV is approximately 19.3 kb, divided into twelve open reading frames (ORFs) (Pappu et al., 1994; Karasev et al., 1995) (FIG. 1). ORF 1a encodes a 349 kDa polyprotein containing two papain-like protease domains plus methyltransferase-like and helicase-like domains. Translation of the polyprotein is thought to occasionally continue through the polymerase-like domain (ORF 1b) by a +1 frameshift. ORFs 1a and 1b plus the nontranslated termini are all that is required for replication in protoplasts (Satyanarayana et al., 1999). Ten 3' ORFs are expressed by 3' co-terminal subgenomic (sg) mRNAs (Hilf et al., 1995; Karasev et al., 1997). In addition to the two coat proteins, p65 (HSP70 homolog) and p61 are required for efficient virion assembly, and are necessary for passage of the virus from protoplast to protoplast in order to amplify inoculum for infection of citrus trees (Satyanarayana et al., 2000). The p6 protein is needed for infection of plants as are the p20 and p23 proteins, which along with CP, are suppressors of RNA silencing (Lu et al., 2004).

CTV can infect and move throughout some citrus varieties with some of the viral genes deleted. CTV contains five genes, p6, p33, p18, p13, and p20, in the 3' half of the genome that are not required for replication or formation of virions. p33, p18 and p13 are not conserved among other members of this virus group, and have been proposed to have evolved for specific interactions with the citrus host. We found that deletions within the p33, p18 or p13 ORF individually resulted in no significant loss of ability of the virus to infect, multiply, and spread throughout citrus trees (Tatineni et al., 2008). Furthermore, deletions in the p33, p18 and p13 genes in all possible combinations including deletions in all three genes allowed the virus to systemically invade citrus trees. Green fluorescent protein-tagged CTV variants with deletions in the p33 ORF or the p33, p18 and p13 ORFs demonstrated that the movement and distribution of these deletion mutants were similar to that of the wild-type virus.

Superinfection exclusion or homologous interference is a phenomenon in which a preexisting viral infection prevents a secondary infection with the same or closely-related virus, whereas infection by unrelated viruses can be unaffected. The phenomenon was first observed by McKinney (McKinney, 1926; 1929) between two genotypes of Tobacco mosaic virus (TMV) and later with bacteriophages (Dulbecco, 1952; Visconti, 1953). Since that time, the phenomenon has been observed often for viruses of animals (Adams and Brown, 1985; Bratt and Rubin, 1968; Delwart and Panganiban, 1989; Geib et al., 2003; Johnston et al., 1974; Karpf et al., 1997; Lee et al., 2005; Singh et al., 1997; Steck and Rubin, 1966; Strauss and Strauss, 1994; Whitaker-Dowling et al., 1983; Wildum et al., 2006) and plants (Bennett, 1951; Fulton, 1978; Gal-On and Shiboleth, 2005; Hull and Plaskitt, 1970; Hull, 2002; Lecoq et al., 1991; Salaman, 1933; Walkey et al., 1992). In plant virology, homologous interference initially was used as a test of virus relatedness to define whether two virus isolates were 'strains' of the same virus or represented different viruses (McKinney, 1929; Salaman, 1933). Subsequently, it was developed into a management tool to reduce crop losses by purposely infecting plants with mild isolates of a virus to reduce infection and losses due to more severe isolates, which is referred to as 'cross-protection' (reviewed in Gal-On and Shiboleth, 2005 and Hull, 2002).

BRIEF DESCRIPTION OF DRAWINGS

FIG. 1(A)—Schematic diagram of the genome organization of wild type CTV T36 (T36 CTV9R). (B) and (C) Schematic representation of the delta p33 CTV construct and the hybrid construct with the substitution of the leader proteases region, respectively. The open boxes represent ORFs and their translation products. PRO, papain-like protease domain; MT, methyltransferase; HEL, helicase; RdRp, an RNA-dependent RNA polymerase; HSP70h, HSP70 homolog; CPm, minor coat protein; CP, major coat protein.

Black box indicates the T68-1 sequence substituted within the T36 genome, respectively. Arrow shows position of the p33 ORF deletion.

Figure 2:
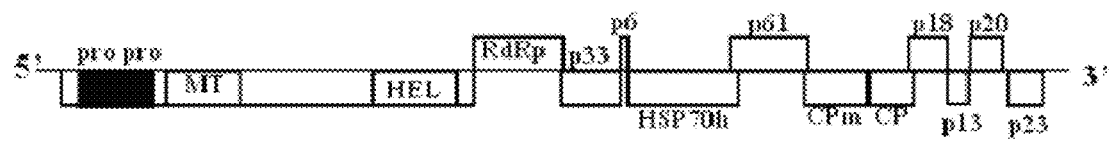
Figure 2:
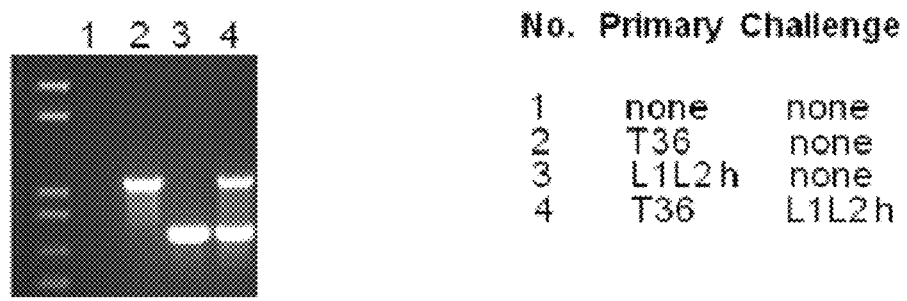

FIG. 2—Scheme of the hybrid virus with the substitution of the proteases region from T68-1 isolate (black box) into the T36 genome. Below: Detection of virus multiplication in plants infected with the T36 isolate or with the hybrid L1L2h alone (lanes 2, 3); lane 4 demonstrates multiplication of L1L2h in plants pre-infected with T36. Virus amplification was analyzed via reverse transcription-PCR reaction with the 2 sets of primers in each reaction mix: one set specific to the proteases region of T36, the other—the proteases region of T68 to discriminate between T36 and L1L2h.

DETAILED DESCRIPTION

Viruses tend to prevent superinfection by related viruses. The addition of a virus-based transient vector normally would prevent application of that or a related vector to the same trees. The inventors also now realize that there are occasions in which it would be valuable to have the ability to add the vector to the target organism (e.g. tree or plant) after such target organism had already been infected with a similar vector. For example, it has come to the attention of the inventors that it would be valuable to be able to add vectors if the vector in a plant has lost the foreign gene being expressed; if a more beneficial gene has been found to express in trees; and/or if more than one gene needs to be expressed. Also, it has come to the realization of the inventors that it is desirous to be able to administer a vector of viral strain to a plant already infected with a wild-type of that strain. The inventors have discovered that targeted modifications within certain portions of a viral vector can avoid the superinfection exclusion phenomenon.

Described herein for certain embodiments of the invention are virus constructs engineered based on Citrus tristeza virus (CTV), a positive-sense RNA closterovirus, that are capable of superinfection in plants that have been infected with a virus of a similar strain. The inventors have discovered that virus constructs engineered via modification of the wild type CTV virus such as they contain a leader protease substituted with a leader protease sequence of different viral strain are able to overcome superinfection exclusion.

According to other certain embodiments, the invention pertains to virus constructs engineered based on Citrus tristeza virus (CTV), a positive-sense RNA closterovirus, that are capable of enabling superinfection of subsequent introduced CTV-based virus construct. The inventors have discovered that virus constructs engineered via modification of the wild type CTV virus such as they lack the gene for the functional p33 protein fail to provide protection against the wild type virus infection. When virus construct lacking p33 protein and the wild type CTV were used for sequential plant inoculation, the primary infection of plants with the deletion mutant virus construct had no noticeable effect on the establishment of the secondary infection by the wild type virus. Thus, deletion of the p33 ORF resulted in a "non-cross-protecting" variant of CTV.

Previously, the inventors examined relationships between different genotypes of Citrus tristeza virus (CTV) in terms of their ability to prevent superinfection by another isolate of the virus. They showed that superinfection exclusion occurred only between isolates of the same CTV strain. When isolates of the same strain were used for sequential plant inoculation, the primary infection provided full exclusion of the challenge isolate. One of the examples of complete cross-protection between CTV viruses noted was full inhibition of GFP-expressing CTV infection in plants pre-infected with the wild-type CTV belonging to the same T36 strain.

According to one embodiment, the inventors examined superinfection exclusion of virus constructs engineered based on infectious cDNA clone of T36 strain of CTV. It was shown that virus constructs engineered via modification of the wild type CTV virus, such as lacking the gene for the functional p33 protein or containing a substitution of the leader protease region from another CTV strain (T68), fail to provide superinfection exclusion of the wild type virus infection. When either of those virus constructs was used for initial inoculation of citrus trees followed by sequential plant inoculation with the wild type CTV, the primary infection of plants with the mutant virus constructs had no noticeable effect on the establishment of the secondary infection by the wild type virus. Thus, deletion of the p33 ORF as well as substitution of the leader protease region resulted in "non-cross-protecting" variants of CTV. Those constructs can potentially be used as vectors for trees that allow multiple applications.

In another embodiment, the invention pertains to a viral vector construct, wherein the construct is engineered to have a leader protease from an isolate of a different strain of a common viral species substituted for the endogenous leader protease of the viral vector. Strains of CTV are defined as phylogenetically distinct lineages of the virus based upon analysis of nucleotide sequences of the 1a ORF (Hilf et al., 2005). Using this definition, T36 and T68 are designated as strains. Individual virus samples are designated as isolates of one of these strains. Each strain is named after a 'type isolate' and is composed of isolates with minor sequence divergence from the type member. In a more specific embodiment, the viral vector is an isolate of CTV that has substituted therein a leader protease sequence from an isolate of a different strain of CTV. In an even more specific embodiment, the CTV vector is engineered based on isolate of T36 strain in which its leader protease sequence is substituted by a leader protease sequence of an isolate of the T68 CTV strain. In a more specific embodiment, the substituted protease sequence is a papain-like protease domain.

According to another embodiment, the inventions pertain to a method of alleviating superinfection exclusion of CTV viral vectors brought about by successive inoculations of viruses. The method includes inoculating a target plant with a first CTV viral vector having a p33 ORF omitted or disrupted, allowing the first CTV viral vector to infect the target plant thereby to produce an infected plant, and then subsequently inoculating the infected plant with a second CTV viral vector that either comprises or does not comprise a p33 gene or disrupted p33 gene. The second CTV viral vector is allowed to infect the already pre-infected plant. In a specific embodiment, the target plant is a citrus tree. In another specific embodiment, the first and/or second CTV vector is engineered to include an expressible sequence encoding a heterologous protein.

According to another embodiment, the inventions pertain to a method of alleviating superinfection exclusion of viral vectors brought about by successive inoculations of viruses. The method includes successively inoculating a target organism with a first and second viral vector. The first viral vector is engineered such that a leader protease sequence is modified by substitution with a cognate leader protease sequence from an isolate of another CTV strain. In a specific embodiment, the first and second viral vectors are derived from a common viral species. In an even more specific embodiment, the first and second viral vectors contain leader protease regions from isolates of different strains of CTV. In a specific embodiment, the target organism is a plant, and in even more specific embodiments a tree, and in even more specific embodiments, a citrus tree. In another specific embodiment, the first and/or second CTV vector is engineered to include an expressible sequence encoding a heterologous protein.

The inventors have realized that there are occasions in which it would be valuable to have the ability to add the vector to the target organism (e.g. tree or plant) after such target organism had already been infected with a similar vector. For example, it has come to the attention of the inventors that it would be valuable to be able to add vectors if the vector in a plant has lost the foreign gene being expressed; if a more beneficial gene has been found to express in trees; and/or if more than one gene needs to be expressed. Also, it has come to the realization of the inventors that it is desirous to be able to administer a vector of viral strain to a plant already infected with a wild-type of that strain. Accordingly, the inventors have discovered that targeted modifications within certain portions of a viral vector can avoid the superinfection exclusion phenomenon.

The inventors have discovered that virus constructs engineered via modification of the wild type CTV virus, such as containing a leader protease substituted with a leader protease sequence of different viral strain, are able to overcome superinfection exclusion.

Relationships between different genotypes of Citrus tristeza virus (CTV) in terms of their ability to prevent superinfection by another isolate of the virus were examined. It was shown that superinfection exclusion occurred only between isolates of the same CTV strain. When isolates of the same strain were used for sequential plant inoculation, the primary infection provided full exclusion of the challenge isolate. One of the examples of complete cross-protection between CTV viruses noted was full inhibition of GFP-expressing CTV infection in plants pre-infected with the wild-type CTV belonging to the same T36 strain (Folimonova et al., 2010).

According to one embodiment, the inventors examined superinfection exclusion of virus constructs engineered based on infectious cDNA clone of T36 strain of CTV. It was shown that virus constructs engineered via modification of the wild type CTV virus, such as they contain substitution of the L1L2 protease region with a cognate sequence from a different viral strain, enable the engineered viral vector to avoid superinfection exclusion even in plants already infected with the same strain of the virus. Accordingly, viral vector embodiments of the present invention can be utilized as vectors for trees pre-infected with the virus of the same strain, such as trees grown in the field that became infected via natural transmission of the virus or trees that became infected as a result of earlier application of a CTV vector engineered based on the same virus strain, to avoid exclusion of the secondary viral vector infection.

In another embodiment, the invention pertains to a viral vector construct, wherein the construct is engineered to have a leader protease from an isolate of a different strain of a common viral species substituted for the endogenous leader protease of the viral vector. Strains of CTV are defined as phylogenetically distinct lineages of the virus based upon analysis of nucleotide sequences of the 1a ORF (Hilf et al., 2005). Using this definition, T36 and T68 are designated as strains. Individual virus samples are designated as isolates of one of these strains. Each strain is named after a 'type isolate' and is composed of isolates with minor sequence divergence from the type member. In a more specific embodiment, the viral vector is an isolate of CTV that has substituted therein a leader protease sequence from an isolate of a different strain of CTV. In an even more specific embodiment, the CTV vector is engineered based on isolate of the T36 strain in which its leader protease sequence is substituted by a leader protease sequence of an isolate of the T68 CTV strain. In a more specific embodiment, the substituted protease sequence is the L1L2 domain.

According to another embodiment, the invention pertains to a method of alleviating superinfection exclusion of CTV viral vectors brought about by successive inoculations of viruses. In a specific embodiment, the method may include inoculating a target plant with a first CTV viral vector engineered based on a first strain of CTV, allowing the first CTV viral vector to infect the target plant thereby to produce an infected plant, and then subsequently inoculating the infected plant with a second CTV viral vector built based on the same CTV strain but which has been modified to include a leader protease sequence of a different (second) strain of the virus. The second CTV viral vector may also include a gene of interest that expresses a protein intended to achieve a beneficial effect. In a specific embodiment, the first strain is T36 and the second strain is T68. The second CTV viral vector is allowed to infect the already pre-infected plant. In a specific embodiment, the target plant is a citrus tree. In another specific embodiment, the first and/or second CTV vector is engineered to include an expressible sequence encoding a heterologous protein.

According to another embodiment, the inventions pertain to a method of alleviating superinfection exclusion of viral vectors. The method includes inoculating a target organism with a viral vector of a strain that has already infected the target organism. The second viral vector is engineered such that a leader protease sequence is modified by substitution with a cognate leader protease sequence from an isolate of another CTV strain. In a specific embodiment, the first and second viral vectors are derived from a common viral species. In an even more specific embodiment, the first and second viral vectors contain leader protease regions from isolates of different strains of CTV. In a more specific embodiment, the leader protease sequence comprises a fragment of a full leader protease sequence comprising 800 base pairs (bp) or less, 700 bp or less, 600 bp or less, 500 bp or less, 400 bp or less, 300 bp or less, 200 bp or less, or 100 bp or less. Alternatively, the vector comprises at least a 100 bp, 200 bp, 300 bp, 400 bp, or 500 bp fragment of a full leader protease sequence. A non-limiting description of examples of known leader protease sequences are discussed in the references section below. In a specific embodiment, the target organism is a plant, and in even more specific embodiments a tree, and in even more specific embodiments, a citrus tree. In another specific embodiment, the first and/or second CTV vector is engineered to include an expressible sequence encoding a heterologous protein.

As used herein, a virus species is a population of viruses with similar characteristics plus which infect the same (or nearly so) range of host species. Reference to "viral strain(s)," refers to a virus classified under a species such as CTV, or other viral species, but which possess gene sequences, or some other characteristic, that are identifiably different from another virus classified under the same species.

EXAMPLES

Example 1

CTV Delta p33 Construct

The inventors examined several virus constructs all containing deletion of the p33 ORF that have been engineered previously based on the infectious cDNA clone of the T36 CTV (Tatineni et al., 2008) for their ability to prevent superinfection of the GFP-expressing CTV. Those deletion mutants have been shown to be able to multiply in and systemically invade trees of most citrus varieties (Tatineni et al., 2008). To assess the effect of a primary infection of a host plant with p33 deletion mutant of CTV on the ability of the GFP-tagged CTV to establish superinfection in the same host, small *Citrus macrophylla* trees were first inoculated with the mutant virus. As a control for this experiment, another set of plants was inoculated with the wild type CTV, see FIG. 1 which shows a schematic representation of the wild type CTV (A) and the p33 deletion mutant construct (B). For both sets, the primary infections were established by grafting virus-infected tissue into the stem of the trees. The upper leaves were trimmed to force the growth of a new set of leaves. At six weeks after inoculation, systemic infections of the new leaves were confirmed by ELISA. The plants were then challenged by inserting a second graft of bark tissue containing the CTV-BC5/GFP. When the graft healed, the upper leaves again were trimmed to induce another new flush of growth. After the development of the second set of new leaves (starting about 6 weeks) the ability of the challenging virus to superinfect trees was determined by visual observation of GFP fluorescence in the bark tissue of the new flush. As a result, the wild type CTV completely prevented superinfection by the GFP-expressing virus: no GFP fluorescence was detected in plants primarily infected with the CTV9R. In contrast, plants that had primary infections with the mutant virus lacking functional p33 protein all displayed GFP fluorescence similar to that observed in plants that had no primary infection and were inoculated only with the challenge virus CTV-BC5/GFP, indicating that the deletion mutant had no interference with infection by the GFP-tagged CTV.

Example 2

CTV Construct with Substitution of the Leader Proteases Region

In a similar experiment, inventors examined hybrid virus constructs in which leader proteases region (nucleotide positions 108-3040 in the CTV genome) has been substituted with the corresponding region of the T68-1 genome, while the rest of the hybrid construct contained sequence of T36 (schematic representation of the construct is given in FIG. 1(C)). T68-1 represents an isolate of T68 strain of CTV. Similarly to the experiment described above, the construct has been used for initial inoculation of citrus plants, which later (upon confirmation of the establishment of the infection by ELISA) were challenged with CTV-BC5/GFP. Wild type CTV was used for primary inoculation of the control trees (as in the above experiment). Starting at 6 weeks after challenge inoculation the ability of the challenging virus to superinfect trees was determined by visual observation of GFP fluorescence in the bark tissue of the new flush. As it was expected, the wild type CTV completely prevented superinfection by the GFP-expressing virus: no GFP fluorescence was detected in plants primarily infected with the CTV9R. In contrast, plants that had primary infections with the hybrid virus carrying substitution of the leader protease region showed GFP fluorescence similar to that observed in plants that had no primary infection and were inoculated only with the challenge virus CTV-BC5/GFP, indicating that this hybrid virus had no interference with infection by the GFP-tagged CTV.

Example 3

Virus with the Substitution of the Protease Region Overcomes Exclusion

Recently it was examined whether modification of the leader proteases region would provide the ability of the virus to overcome exclusion. We engineered a hybrid virus construct in which a region in the T36 cDNA clone containing two leader proteases L1 and L2 (nts positions 108-3039 in the CTV genome) has been substituted with the corresponding region from the genome of T68-1 isolate of the T68 strain, while the rest of the hybrid construct contained sequence of T36 (FIG. 2). The described virus construct was used for challenge-inoculation of plants primary infected with the parental T36 CTV virus. As we demonstrated earlier, primary infection with an isolate of CTV completely excludes infection with another isolate of the same strain. For example, infection with an isolate of T36 strain excluded secondary infection with other isolates of T36 strain as well as excluded infection with the T36-based GFP-tagged virus. Moreover, infection with the T36 isolate fully excluded secondary infections by the hybrid viruses constructed based on the T36 isolate in which sequences of 8 genes in the 3' half of the genome were substituted (sequences of individual genes or several genes in combinations) with the corresponding sequences from isolates of the T30 or T68 strains. Remarkably, the hybrid virus with the T68 leader proteases region substituted into the T36 genome demonstrated a unique behavior: the mutant virus was able to systemically infect plants pre-infected with the parental T36 virus, showing levels of virus accumulation similar to the levels of the same virus when inoculated into healthy plants (FIG. 1; compare lane 4 to the other lanes from control inoculations).

REFERENCES

Adams, R. H., and D. T. Brown. 1985. BHK cells expressing Sindbis Virus-induced homologous interference allow the translation of nonstructural genes of superinfecting virus. J. Virol. 54:351-357.

Bratt, M. A., and H. Rubin. 1968. Specific interference among strains of Newcastle disease virus 3 Mechanism of interference. Virology 35: 395-407.

Dawson, W. O., Lewandowski, D. J., Hilf, M. E., Bubrick, P., Raffo, A. J., Shaw, J. J., Grantham, G. L., Desjardins, P. R., 1989. A Tobacco mosaic virus-hybrid expresses and loses an added gene. Virology 172, 285-292.

Delwart, E. L., and A. T. Panganiban. 1989. Role of reticuloendotheliosis virus envelope glycoprotein in superinfection interference. J. Virol. 63:273-280.

Donson, J., Kearney, C. M., Hilf, M. E., Dawson, W. O., 1991. Systemic expression of a bacterial gene by a Tobacco mosaic virus-based vector. Proc. Natl. Acad. Sci. USA 88, 7204-7208.

Dulbecco, R. 1952. Mutual exclusion between related phages. J. Bacteriol. 63:209-217.

Fulton, R. W. 1978. Superinfection by strains of tobacco streak virus. Virology 85:1-8.

Gal-On, A., and Y. M. Shiboleth, 2005. Cross protection, p. 261-288. In G. Loebenstein and J. P. Carr (ed.). Natural resistance mechanisms of plants to viruses. Springer, Dordrecht, The Netherlands.

Geib, T., C. Sauder, S. Venturelli, S. Hassler, P. Staeheli, and M. Schwemmle. 2003. selective virus resistance conferred by expression of borna disease virus nucleocapsid components. J. Virol. 77:4283-4290.

Hilf, M. E., Karasev, A. V., Pappu, H. R., Gumpf, D. J., Niblett, C. L., Garnsey, S. M., 1995. Characterization of Citrus tristeza virus subgenomic RNAs in infected tissue. Virology 208, 576-582.

Hilf, M. E., V. A. Mavrodieva, and S. M. Garnsey. 2005. Genetic marker analysis of a global collection of isolates of Citrus tristeza virus: Characterization and distribution of CTV genotypes and association with symptoms. Phytopathology 95:909-917.

Hull, R., and A. Plaskitt. 1970. Electron microscopy on the behaviour of two strains of alfalfa mosaic virus in mixed infections. Virology 42:773-776.

Hull, R. 2002. Matthews' Plant Virology. Academic Press, New York.

Johnston, R. E. K. Wan, and H. R. Bose. 1974. Homologous interference induced by Sindbis virus. J. Virol. 14:1076-1082.

Karasev, A. V., 2000. Genetic diversity and evolution of closteroviruses. Annu. Rev. Phytopathol. 38, 293-324.

Karasev, A. V., Boyko, V. P., Gowda, S., Nikolaeva, O. V., Hilf, M. E., Koonin, E. V., Niblett, C. L., Cline, K., Gumpf, D. J., Lee, R. F., Garnsey, S. M., Lewandowski, D. J., Dawson, W. O., 1995. Complete sequence of the Citrus tristeza virus RNA genome. Virology 208, 511-520. This reference teaches portions of the CTV virus including the leader protease sequence. It is incorporated herein to show an example of the sequences that can be replaced in one genome of a first isolate with cognate sequences in another isolate. See also Genbank Accession Nos. EU937521.1; AF001623.1; DQ272579.1 for sequence information on the CTV genome of different strains.

Karpf, A. R., E. Lenches, E. G. Strauss, J. H. Strauss, and D. T. Brown. 1997. Superinfection exclusion of alphaviruses in three mosquito cell lines persistently infected with Sindbis virus. J. Virol. 71:7119-7123.

Lecoq, H., J. M. Lemaire, and C. Wipf-Scheibel. 1991. Control of zucchini yellow mosaic virus in squash by cross protection. Plant Dis. 75:208-211.

Lee Y. M., D. M. Tscherne, S. I. Yun, I. Frolov, and C. M. Rice. 2005. Dual mechanisms of pestiviral superinfection exclusion at entry and RNA replication. J. Virol. 79:3231-3242.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc. Natl. Acad. Sci. USA 101, 15742-15747.

McKinney, H. H. 1926. Virus mixtures that may not be detected in young tobacco plants. Phytopathology 16:893.

McKinney, H. H. 1929. Mosaic diseases in the Canary Islands, West Africa and Gibraltar. J. Agric. Res. 39:557-578.

Pappu, H. R., Karasev, A. V., Anderson, E. J., Pappu, S. S., Hilf, M. E., Febres, V. J., Eckloff, R. M. G., McCaffery, M., Boyko, V., Gowda, S., Dolia, V. V., Koonin, E. V., Gumpf, D. J., Cline, K. C., Garnsey, S. M., Dawson, W. O., Lee, R. F., Niblett, C. L., 1994. Nucleotide sequence and organization of eight 3' open reading frames of the Citrus tristeza closterovirus genome. Virology 199, 35-46.

Rabindran, S., Dawson, W. O., 2001. Assessment of recombinants that arise from the use of a TMV-based transient expression vector. Virology 284, 182-189.

Salaman, R. N. 1933. Protective inoculation against a plant virus. Nature (London) 131:468.

Satyanarayana, T., Gowda, S., Boyko, V. P., Albiach-Martì, M. R., Mawassi, M., Navas-Castillo, J., Karasev, A. V., Dolja, V., Hilf, M. E., Lewandowski, D. J., Moreno, P., Bar-Joseph, M., Garnsey, S. M., Dawson, W. O., 1999. An engineered closterovirus RNA replicon and analysis of heterologous terminal sequences for replication. Proc. Natl. Acad. Sci. USA 96, 7433-7438.

Satyanarayana, T., Gowda, S., Mawassi, M., Albiach-Martì, M. R., Ayllón, M. A., Robertson, C., Garnsey, S. M., Dawson, W. O., 2000. Closterovirus encoded HSP70 homolog and p61 in addition to both coat proteins function in efficient virion assembly. Virology 278, 253-265.

Satyanarayana, T., Bar-Joseph, M., Mawassi, M., Albiach-Martì, M. R., Ayllón, M. A., Gowda, S., Hilf, M. E., Moreno, P., Garnsey, S. M., Dawson, W. O., 2001. Amplification of Citrus tristeza virus from a cDNA clone and infection of citrus trees. Virology 280, 87-96.

Satyanarayana, T., Gowda, S., Ayllón, M. A., Albiach-Martì, M. R., Rabindran, S., Dawson, W. O., 2002. The p23 protein of Citrus tristeza virus controls asymmetrical RNA accumulation. J. Virol. 76, 473-483.

Satyanarayana, T., Gowda, S., Ayllón, M. A., Dawson, W. O., 2003. Frameshift mutations in infectious cDNA clones of Citrus tristeza virus: a strategy to minimize the toxicity of viral sequences to *Escherichia coli*. Virology 313, 481-491.

Shivprasad, S., Pogue, G. P., Lewandowski, D. J., Hidalgo, J., Donson, J., Grill, L. K., Dawson, W. O., 1999. Heterologous sequences greatly affect foreign gene expression in Tobacco mosaic virus-based vectors. Virology 255, 312-323.

Singh, I. R., M. Suomalainen, S. Varadarajan, H. Garoff, and A. Helenius. 1997. Mechanisms for the inhibition of entry and uncoating of superinfecting Semliki forest virus. Virology 231:59-71.

Steck, F. T., and H. Rubin. 1966. The mechanism of interference between an Avian leukosis virus and Rous sarcoma virus, I establishment of interference. Virology 29:628-641.

Strauss, J. H., and E. G. Strauss. 1994. The alphaviruses: gene expression, replication, and evolution. Microbiol. Rev. 58:491-562.

Tatineni, S., Robertson, C. J., Garnsey, S. M., Bar-Joseph, M., Gowda, S., and Dawson, W. O. 2008. Three genes of Citrus tristeza virus are dispensable for infection and movement throughout citrus trees. Virology 376: 297-307.

Visconti, N. 1953. Resistance to lysis from without in bacteria infected with T2 bacteriophage. J. Bacteriol. 66:247-253.

Walkey, D. G. A., H. Lecoq, R. Collier, and S. Dobson. 1992. Studies on the control of zucchini yellow mosaic virus in courgettes by mild strain protection. Plant Pathol. 41:762-771.

Whitaker-Dowling, P. A., J. S. Youngner, C. C. Widnell, and D. K. Wilcox. 1983. Superinfection exclusion by vesicular stomatitis virus I. Virology 131:137-143.

Wildum, S. M., M. Schindler, J. Munch, and F. Kirchhoff. 2006. Contribution of Vpu, Env, and Nef to CD4 downmodulation and resistance of human immunodeficiency virus type I-infected T cells to superinfection. J. Virol. 80:8047-8059.

Also, see Foliminova et al., J. Virol. (2010) 84:1314-1325, for disclosure on making viral constructs and using same for infection in plants.

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

What is claimed is:

1. A method of alleviating superinfection exclusion of Citrus tristeza virus (CTV) viral vectors associated with successive transfections of CTV viruses to a citrus tree, said method comprising: inoculating the citrus tree with a first CTV viral vector being of a CTV strain T36 engineered to have a L1L2 leader protease region substituted with a cognate region from an isolate of T68 strain of CTV; allowing the first CTV viral vector to infect the citrus tree thereby to produce a primarily infected citrus tree, and inoculating the primarily infected citrus tree with a second CTV viral vector whereby the second CTV viral vector further infects the primarily infected citrus tree to produce a secondarily infected citrus tree, wherein the second CTV vector is engineered to include an expressible sequence encoding a heterologous protein; and wherein the second CTV viral vector is T36 strain of CTV.

* * * * *